United States Patent [19]

Schrott et al.

[11] Patent Number: 4,806,664
[45] Date of Patent: Feb. 21, 1989

[54] NOVEL TETRAPHENYLDITHIOLENE COMPLEXES, ASYMMETRICALLY SUBSTITUTED BENZOINS, AND OPTICAL RECORDING MATERIALS CONTAINING THE NOVEL COMPLEXES

[75] Inventors: Wolfgang Schrott, Ludwigshafen; Peter Neumann, Wiesloch; Bernhard Albert, Maxdorf; Michael Thomas, Weisenheim am Berg; Helmut Barzynski, Bad Durkheim; Klaus-Dieter Schomann, Ludwigshafen; Harald Kuppelmaier, Heidelberg, all of Fed. Rep. of Germany

[73] Assignee: BASF Aktiengesellschaft, Ludwigshafen, Fed. Rep. of Germany

[21] Appl. No.: 57,640

[22] Filed: Jun. 8, 1987

Related U.S. Application Data

[63] Continuation of Ser. No. 831,414, Feb. 20, 1986, abandoned.

[30] Foreign Application Priority Data

Feb. 20, 1985 [DE] Fed. Rep. of Germany ....... 3505751

[51] Int. Cl.$^4$ .......................... G03C 1/50; G03C 1/72; C07F 17/02
[52] U.S. Cl. ................................... 556/136; 556/146; 430/945; 430/944; 430/270
[58] Field of Search ...................... 430/945, 944, 270; 556/146, 136

[56] References Cited

U.S. PATENT DOCUMENTS 4,219,826 8/1980 Bloom et al. .................. 430/945 X
4,320,489 3/1982 Crandall et al. .................. 346/76 L Primary Examiner—Won H. Louie
Assistant Examiner—Cynthia Hamilton
Attorney, Agent, or Firm—Oblon, Fisher, Spivak, McClelland & Maier

[57] ABSTRACT

Tetraphenyldithiolene complexes of the formula

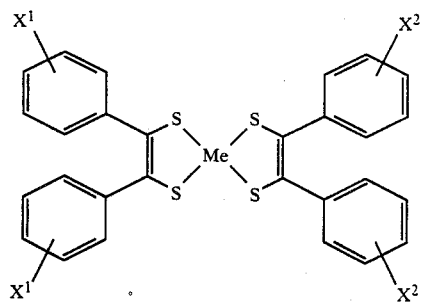

and novel asymmetrically substituted benzoins of the formula

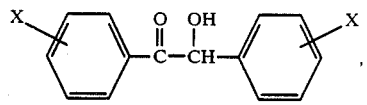

where $X^1$, $X^2$ and X have the meanings stated in the description and Me is nickel, palladium or platinum. The complexes have very high absorption in the range from 800 to 950 nm and are readily soluble in the plastics used for the production of optical recording materials.

The recording materials produced using these complexes have a very high signal/noise ratio.

6 Claims, No Drawings

NOVEL TETRAPHENYLDITHIOLENE COMPLEXES, ASYMMETRICALLY SUBSTITUTED BENZOINS, AND OPTICAL RECORDING MATERIALS CONTAINING THE NOVEL COMPLEXES

This application is a continuation of application Ser. No. 831,414, filed on Feb. 20, 1986, now abandoned.

BACKGROUND OF THE INVENTION

1. Field of the Invention

The present invention relates to novel tetraphenyldithiolene complexes, asymmetrically substituted benzoins as intermediates for their preparation, and an optical recording material which contains the novel tetraphenyldithiolene complexes.

2. Discussion of the Background

Recording materials in which radiation having a high energy density, eg. laser light, produces a localized change of state are known. This thermally produced change of state, for example vaporization, change in flow behavior or fading, is associated with a change in the optical properties, for example in the absorption as a result of a change in the absorption maximum, or in the extinction, and this change can be utilized for recording information or data.

Because of the small size of the element, its low energy demand and the possibility of direct modulation of the optical output power by modulating the electric driving current, solid state injection lasers which emit in the near infrared, especially the AlGaAs laser, which operates in the wavelength range from about 750 to 950 nm, are particularly useful as a light source for an optical recording system.

A large number of inorganic and organic materials are known for this application. These materials have an adequate absorption in this wavelength range and alter their optical properties by absorbing the radiation and hence the energy present therein in the stated wavelength range, by disintegration, vaporization, melting or in another manner.

The known information recording materials consist of a base on which thin layers of inorganic materials, eg. metals, semimetals, alloys or chalcogen glass, or organic compounds, such as IR dyes, are applied. The thin layers are produced, in particular, by vapor deposition under reduced pressure or by atomization techniques. The thickness of the layers should be chosen so that the total incident radiation is absorbed, unless it is intended to utilize intereference phenomena. The base can consist of glass or of suitable plastics, eg. a polycarbonate, polymethylmethacrylate, polystyrene, a polystyrene copolymer, polyvinyl chloride or polymethylpentene.

When used as a storage material, the amorphous layers must remain unchanged over prolonged periods. Aging processes, eg. crystallization or fading due to light and heat, which alter the morphology of the storage layer take place relatively frequently in thin layers produced by vapor deposition. Neutral IR dyes in polymer films, ionic IR dyes in the form of lakes or IR chromophores chemically bonded to polymers should be more stable over prolonged periods. Moreover, the latter have the advantage that they can be prepared by a more economical process.

A large number of bases, reflective materials and laser light-sensitive layers for optical recording materials for use with semiconductor injection lasers are known. Organic IR dyes described are, in particular, phthalocyanine compounds, methine dyes and quadratic acid derivatives. Complex azo dyes, anthraquinone dyes and triphenylmethane dyes as well as pyrylium and thiopyrylium salts have likewise been described but only have a reStricted use since their absorption maximum in most cases is at too short a wavelength for the conventional semiconductor lasers. This problem does not arise in the case of the dithiolene complexes, a large number of which are known [for example, J. A. McCLEVERTY, Progr. Inorg. Chem. 10, (1968), 49-221; G. N. SCHRAUZER, Acc. Chem. Res. 2, (1969), 72-80] and whose use in optical recording materials has been described.

WO No. 83/02 428 describes an optical recording material which contains nickel-benzodithiolene complexes of the formula

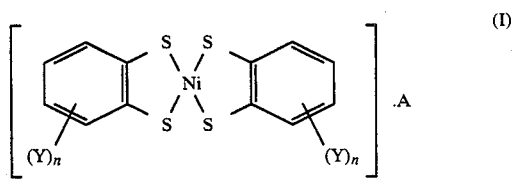

where X is hydrogen, 1-methyl, 1,4-dimethyl, 1,2,3,4-tetramethyl, 1-chloro or 1,2,3,4-tetrachloro and A is a tetraalkylammonium cation. These complexes absorb between 800 and 950 nm ($\epsilon$ less than 17,000).

DE-A No. 2 951 341 descloses a recording medium which can be writren on by means of an AlGaAs laser and carries, on a glass substrate, a light-reflecting layer, eg. gold, and a light-absorbing layer. The layers are produced on the substrate by vapor deposition under reduced pressure. The light-absorbing layer consists of dithiolene complexes of the formula

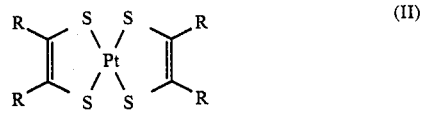

where R is unsubstituted or substituted phenyl.

A similar system is described in U.S. Pat. No. 4,320,489 and takes the form of a reversible optical recording medium which possesses on the surface, as a photosensitive layer, a thermoplastic layer which contains compounds of the formula

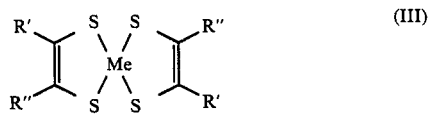

where Me is nickel, palladium or platinum and R' and R" are each alkyl or unsubstituted or substituted phenyl. However, no information is given regarding the quality of the recording medium, for example in the form of read or write energies or signal-to-noise ratios.

When other IR dyes of the formula (III) which are disclosed in the literature were used, it was found that these IR dyes are not sufficiently soluble iri the polymers used, so that the recording media produced with them, although capable of being written on, were of unsatisfactory quality.

Our own experiments have wshown that all known dithiolene complexes and the other, very pure dithiolene complexes stated above and mixtures of these compounds, which can be deposited as a thin layer on a base by vapor deposition under reduced pressure, crystallized more or less rapidly after vapor deposition or after further exposure to heat, with the result that these dye layers are useless as a material for an optical recording medium. In addition to the known disadvantages of batchwise vaporization under reduced pressure during mass production, recording media of this type are very unlikely to possess long-term stability.

Res. Discl. 21 612/1982 discloses dithiolene complexes of the formula (III), where the radicals R' independently of one another are each aryl, such as alkylaryl or alkoxyaryl, R'' is hydrogen or unsubstituted or substituted alkyl and Me is nickel. These complexes absorb between about 700 and 900 nm and possess good solubilities in various organic solvents.

SUMMARY OF THE INVENTION

It is an object of the present invention to provide readily soluble IR dyes which are readily soluble in the polymers used for such recording materials and accordingly can be incorporated in high concentrations into thin polymer films, and furthermore possess adequate absorption at the wavelength of the incident light in the polymers used and finally form polymer layers which are amorphous or which possess crystalline regions which are smaller than the wavelength of the incident light.

DESCRIPTION OF THE PREFERRED EMBODIMENTS

We have found that this object is achieved by the novel tetraphenyldithiolene complexes.

The present invention relates to tetraphenyldithiolene complexes of the formula

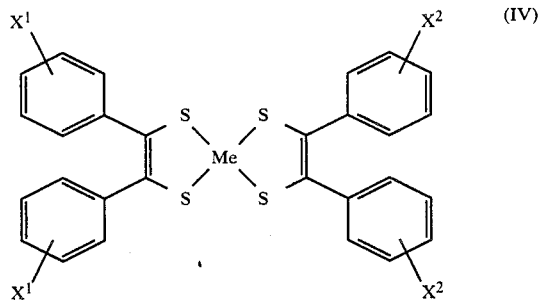

(IV)

where one radical $X^1$ and one radical $X^2$ are each straight-chain or branched $C_5$–$C_{30}$-alkyl in the 4-position, the other radicals $X^1$ and $X^2$ are each hydrogen, $C_1$–$C_{12}$-alkyl, $C_1$–$C_{12}$-alkoxy, fluorine, chlorine or bromine in the 2-, 3- or 4-position, and Me is nickel, palladium or platinum. The dithiolene complexes (IV) can occur in the cis- or trans-form or as a mixture of the two isomers.

The dithiolene complexes according to the present invention have a very high molar absorption ($\epsilon$ as high as 52,000) in the wavelength range for semiconductor laser light of from 750 to 950 nm. They are readily soluble in organic solvents and in polymers and accordingly give amorphous, non-crystalline layers. The storage media obtained using dyes of the formula (IV) are of superior quality, possessing, for example, high optical contrast, a very high signal-to-noise ratio and an advantageous threshold energy.

Specific examples of suitable substituents $X^1$ and $X^2$ are as follows: One radical $X^1$ and one radical $X^2$ are each straight-chain or branched $C_5$–$C_{30}$-alkyl, preferably $C_8$–$C_{24}$-alkyl, these alkyl groups each being in the 4-position. Examples are n-pentyl, n-hexyl, heptyl, n-octyl, 2-ethylhexyl, n-nonyl, n-decyl, n-dodecyl, tridecyl, tetradecyl, pentadecyl, hexadecyl, octadecyl, eicosyl, heneicosyl, docosyl, tetracosyl, pentacosyl, hexacosyl or triacosyl, the radicals from octyl to tetracosyl being preferred.

The other radicals $X^1$ and $X^2$ may each be not only hydrogen, chlorine, fluorine or bromine, but also $C_1$–$C_{12}$-alkyl or $C_1$–$C_{12}$-alkoxy, these radicals being in the 2-, 3- or 4-position.

Examples of $C_1$–$C_{12}$-alkyl, which may be straight-chain or branched, are methyl, ethyl, n- and isopropyl, n- and isobutyl, 2-butyl, tert.-butyl, pentyl, n-hexyl, heptyl, n-octyl, 2-ethylhexyl, nonyl, n-decyl and n-dodecyl.

Examples of suitable $C_1$–$C_{12}$-alkoxy radicals are methoxy, ethoxy, propoxy, n-butoxy, n-pentyloxy, n-hexyloxy, n-octyloxy, 2-ethylhexyloxy, n-nonyloxy, n-decyloxy and n-dodecyloxy.

Where the other radicals $X^1$ and $X^2$ are each alkyl or alkoxy and these radicals are of more than 2 carbon atoms, they are preferably in the 4-position.

The other radicals $X^1$ and $X^2$ are each preferably methyl, ethyl, methoxy, ethoxy, fluorine, chlorine or bromine.

Me is nickel, palladium or platinum. Because of their performance characteristics, the platinum complexes are preferred, these complexes possessing superior optical properties and being very readily soluble in the polymers used for recording materials and accordingly giving excellent recording materials.

The complexes (IV) are prepared from benzoins by conventional methods (G. N. Schrauzer et al., J. Amer. Chem. Soc. 87 (1965), 1483–1489), by thionation followed by precipitation as the metal salt in a single-vessel process:

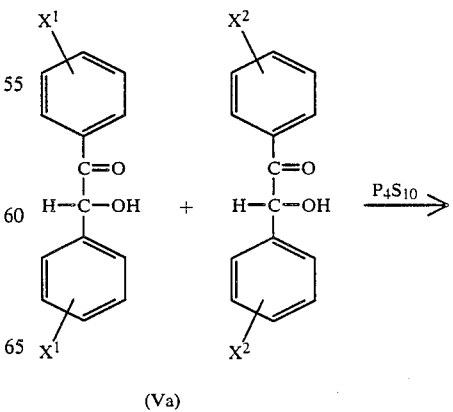

(Va)

-continued

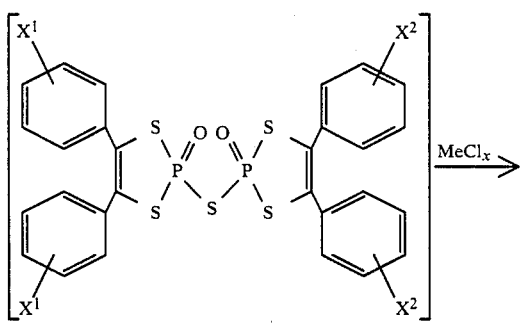

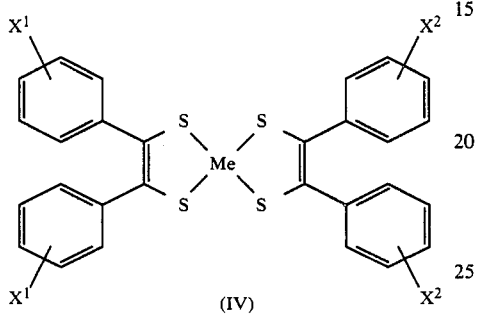

They can also be obtained from the corresponding benzil compounds, although in substantially poorer yields.

The novel asymmetrically substituted benzoins of the formula (V)

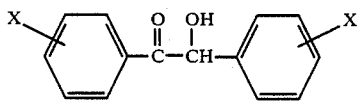

where one radical X is straight-chain or branched $C_5$–$C_{30}$-alkyl in the 4-position and the other radical X is hydrogen $C_1$–$C_{12}$-alkyl, $C_1$–$C_{12}$-alkoxy, fluorine, chlorine or bromine in the 2-, 3- or 4-position, serve as starting materials for the dithiolene complexes of the formula (IV).

Preferred benzoins of the formula (V) are those in which one radical X is $C_8$–$C_{24}$-alkyl and the other radical X is methyl, ethyl, methoxy, ethoxy, fluorine, chlorine or bromine.

The radicals X in formula (V) are identical to the radicals $X^1$ and $X^2$ in the formulae (IV) and (Va).

The novel benzoins of the formula (V), which are also useful intermediates for the synthesis of crop protection agents, drugs and dyes and serve as additives for plastics, are prepared by a conventional method. They are obtained either from unsubstituted or substituted phenylglyoxal and a substituted aromatic [equation (1)] or by reacting an unsubstituted or substituted phenylacetyl chloride with a substituted aromatic and then oxidizing the product [equation (2)]:

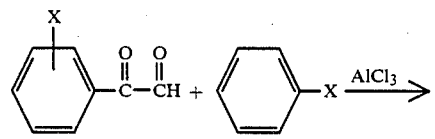

-continued

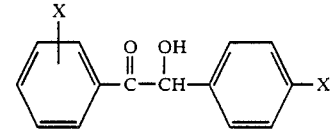

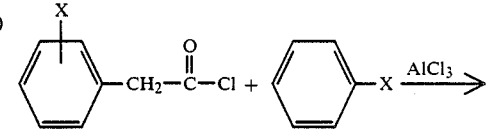

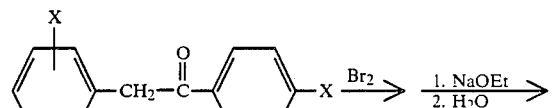

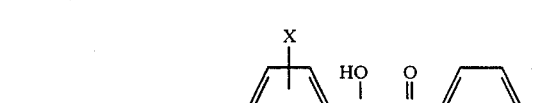

The novel benzoins (V) are obtainable only in poor yields, if at all, by benzoin condensation.

The phenylglyoxals which are substituted in the nucleus and are required as starting materials for process (1) can be prepared from the corresponding acetophenone by oxidation with selenium dioxide by a method similar to that described in Organic Synthesis, Coll. Vol. 2 (1943), 509. The Friedel-Crafts acylation of substituted phenylglyoxals [process (1)] are phenylacetyl chlorides substituted in the nucleus [process (2)] is carried out by modified methods from Organikum, Berlin, 12th edition, 1973, page 354 (cf. the information under A.1 and A.2 below). The benzoins (Vb) are prepared by bromination of the deoxybenzoins followed by hydrolysis, using a modified method dude to S. S. Jenkins, J. Am. Chem. Soc. 56 (1934), 682 (cf. A.2).

The present invention furthermore relates to optical recording materials which comprise a base and a dye-containing layer which is sensitive to laser light and consists of a thermoplastic polymer, wherein the said polymer contains one or more tetraphenyldithiolene complexes of the formula

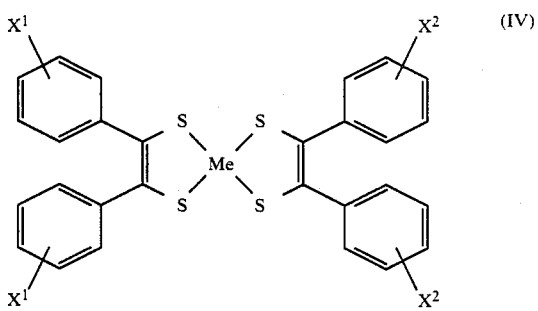

where one radical $X^1$ and one radical $X^2$ are each straight-chain or branched $C_5$–$C_{30}$-alkyl in the 4-position, the other radicals $X^1$ and $X^2$ are each hydrogen, $C_1$–$C_{12}$-alkyl, $C_1$–$C_{12}$-alkoxy, fluorine, chlorine or bromine in the 2-, 3- or 4-position and Me is nickel, palladium or platinum.

The preferred recording layers contain tetraphenyldithiolene complexes of the formula (IV) where one radical $X^1$ and one radical $X^2$ are each $C_8$–$C_{24}$-alkyl and the other radicals $X^1$ and $X^2$ have the above meanings.

Particularly preferred complexes are those in which the other radicals $X^1$ and $X^2$ are each methyl, ethyl, methoxy, ethoxy, fluorine, chlorine or bromine.

Very particularly preferred recording materials contain the components of the formula (IV) in the form of the platinum complexes.

The novel recording systems has a very high absorption at the wavelength of the semiconductor lasers from about 750 to 950 nm. The polymer layers can be applied onto a light-reflecting layer so as to give smooth absorption layers of optical quality, into which the information to be stored can be written with a high Signal-to-noise ratio.

The recording materials according to the present invention are capable of being written on and read by means of a semiconductor laser and are very stable to atmospheric effects and daylight.

Because of the high light absorption of the dyes, the novel recording materials are very sensitive to the llight from a GaAlAs semiconductor laser.

The structure of the recording materials is known per se.

A reflecting layer may be present between the light-absorbing layer and the base, so that the incident light which passes through the colored layer (provided that it is not absorbed) is reflected at the reflector layer and again passes through the colored layer.

Exposure may also be carried out through a transparent substrate, in which case a suitable layer sequence is the following: substrate, absorber layer and, if necessary, reflector layer.

The light-reflecting layer should be such that the light used for recording and for scanning is very quantitatively reflected by this layer. Examples of suitable light-reflecting materials are aluminum, rhodium, gold, tin, lead, bismuth, copper and dielectric mirrors. The thickness of the light-reflecting layer should be sufficiently large for the light used for recording or for scanning to be reflected as completely as possible by this layer.

Mirrors having a low thermal conductivity are advantageous for this purpose. The base, or the light-reflecting layer, must have an optically smooth, flat surface, and the surface must be such that the absorbing layer adheres firmly to it. In order to exert an advantageous influence on the surface quality and adhesion phenomena, the base and/or the reflector may be provided with a subbing layer consisting of a duroplastic or thermoplastic material.

Metallic reflector layers are preferably applied in a conventional manner by vapor deposition under reduced pressure or by applying a suitable metal foil to the base. The novel layer which is sensitive to laser light is preferably applied by whirler-coating with the dissolved or dispersed dye in the presence of a binder. Other suitable methods of producing the layers are knife-coating and immersion.

To apply the absorption layers from solution, a solution or, if necessary, a dispersion of the dye or dye mixture and the polymer in a suitable solvent, such as methylene chloride, chloroform, carbon tetrachloride, acetone, methyl ethyl ketone, cyclohexanone, toluene, acetonitrile, ethyl acetate, methanol or a mixture of these, is prepared, and, if required, a binder is added.

Suitable binders are either radiation-curable or heat-curable resins, eg. photopolymers, silicone resins and epoxy resins or thermoplastics.

Thermoplastics which are non-crystalline or possess only very low crystallinity and have a glass transition temperature of $>35°$ C., in particular $>75°$ C., are preferred. Moreover, the binders, such as resins or thermoplastics, must possess good compatibility with the novel dithiolene compounds (IV). Examples of suitable substances are water-inosluble binders having a high dissolving power for the dithiolene compounds, eg. (meth)acrylate polymers and copolymers, polystyrene homopolymers and copolymers, polyvinylcarbazole, polyvinyl ester copolymers, polyvinyl chloride and cellulose esters.

The dye formulation is then applied onto a previously cleaned or pretreated substrate (subbing layer) by knife-coating, immersion or, preferably, whirler-coating, and the layer is dried or cured in the air. The film may also be dried or cured under reduced pressure, at elevated temperatures or, if necessary, using radiation.

Depending on the structure of the system, the dye-in-polymer layer is first applied and then the reflector, or vice versa. The application of intermediate and protective layers or of a reflecting layer can, if appropriate, be dispensed with.

Where the dye-in-polymer layer does not possess sufficient mechanical stability, it can be covered with a transparent protective layer. This can be done with a number of polymers, which can be used to produce a protective layer by whirler coating, knife coating or immersion using a solution of the polymer or by vapor deposition under reduced pressure, in particular using fluorinated polymers.

When the system (data store) is built up from two identical or different recording materials in the form of a sandwich, a protective layer can be disposed with. Apart from greater mechanical and rotational dynamic stability, the sandwich structure has the advantage of affording twice the storage capacity.

When the optical recording material is of adequate quality, the protective and/or intermediate layers can be dispensed with. Where intermediate layers cannot be dispensed with, the thickness of these layers must be chosen so that no troublesome interference can occur, the refractive index of the material used for this purpose and the wavelength of the laser light employed being taken into account.

The heat generated when the laser light is absorbed results in the thermoplastic flowing radially outward and hence in the formation of holes with sharply defined edges, giving an excellent signal/noise ratio.

The Examples which follow illustrate the invention. Percentages are by weight.

The tetraphenyldithiolene complexes are also referred to below as bisthiobenzil complexes.

A.

PREPARATION LOF THE BENZOIN COMPOUNDS (V)

A.1 Preparation of 4'-n-octylbenzoin (compound V.1)

[Process (1)]

57.0 g (0.30 mole) of n-octylbenzene are dissolved in 800 ml of carbon disulfide, the solution is cooled to 0°

C., 66.5 g (0.50 mole) of aluminum chloride are added, and a solution of 40.0 g (0.30 mole) of phenylglyoxal and 50 ml of carbon disulfide are added dropwise at from 5° to 10° C., while stirring vigorously. The yellow to orange reaction mixture is stirred for a further 15 hours without being cooled, after which it is poured carefully onto 1 l of semiconcentrated ice-cold hydrochloric acid, and the mixture is stirred thoroughly. The phases are separated, the organic phase is extracted by shaking with 300 ml of water, the aqueous phases are extracted with 300 ml of methylene chloride, and the combined organic phases are dried over sodium sulfate. The solution is filtered and the solvent is distilled off to give 75.0 g ($\triangleq$77% of theory) of crude product which has a melting range of 85°–89° C. and is 95% pure according to gas chromatography. Recrystallization from methanol gives analytically pure 4'-n-octylbenzoin.

Mp.: 90°–91° C. (ethanol).

$C_{22}H_{28}O_2$ (324.5) calculated: C 81.5 H 8.5 O 9.9%, found: C 81.5 H 8.6 O 10.1%.

IR: $\nu$=1673 (C=O), 2842 S, 2918 (C—H), 3370, 3415 (O—H) cm$^{-1}$.

MS (70 eV): m/e=324 (M$^\oplus$), 219 (100%, M$^\oplus$—$C_6H_5$—C=O), 105 ($C_6H_5$—CO$^\oplus$).

A.2 Preparation of 4-n-octylbenzoin (compound V.2) [Process (2)]

57.0 g (0.30 mole) of n-octylbenzene are dissolved in 500 ml of carbon disulfide, 45.0 g (0.34 mole) of aluminum chloride are added at 0° C., and a solution of 46.4 g (0.30 mole) of phenylacetyl chloride and 50 ml of carbon disulfide are added dropwise at from 0° to 5° C., while stirring. The reaction mixture is stirred for a further 2 hours at from 0° to 5° C. and then for 15 hours without being cooled, after which it is poured carefully onto 1 l of semiconcentrated ice-cold hydrochloric acid. The phases are separated, the organic phase is extracted by shaking with 300 ml of water, the aqueous phase is extracted with three times 300 ml of methylene chloride, and the combined organic phases are dried over sodium sulfate. The solution is filtered and the solvent is distilled off to give 92 g (=100% of theory) of deoxybenzoin as a colorless crystalline mass, which is shown by thin layer chromatography (silica gel/$CH_2Cl_2$: R$\approx$0.95; toluene: R$\approx$0.61) to be sufficiently pure for the subsequent bromination.

When this procedure is repeated using batches of different sizes, yields of crude product of from 70 to 90% are obtained. In these cases, the crude product has to be recrystallized once from ethanol before the bromination is carried out.

120 g (0.35 mole) of 4-n-octyldeoxybenzoin are dissolved in 500 ml of 1,2,2-trichloro-1,1,2-trifluoroethane. 16 ml (56 g, 0.35 mole) of bromine are added dropwise in the course of one hour, while irradiating with UV light, so that the solution is continuously decolorized. Thereafter, the reaction solution is heated at the boil for one hour, and thin layer chromatography is used to check for complete conversion. The solvent is completely stripped off, 140 g of crude product being obtained as the residue. This is dissolved in 100 ml of ethanol, and a solution of 56.7 g (1.05 moles) of sodium methylate in 200 ml of ethanol is added dropwise at room temperature to the stirred solution, the internal temperature increasing to 35° C. The reaction mixture is stirred for a further 15 hours at room temperature, after which it is discharged onto 1 l of semiconcentrated hydrochloric acid and stirring is continued for about a further 30 minutes. The precipitate is filtered off, washed with water and recrystallized from petroleum ether (60°–80° C.) to give 103.2 g (91% yield) of 4-n-octylbenzoin of melting point 65°–70° C.). According to thin layer chromatography, this product is only slightly contaminated. Column chromatography over silica gel 60 using methylene chloride as the mobile phase gives 70 g (62%) of analytically pure 4-n-octylbenzoin (thin layer chromatography over silica gel/$CH_2Cl_2$: R=0.78; toluene: R=0.18).

Mp.: 74°–75° C.

$C_{22}H_{28}O_2$ (324.5) calculated: C 81.5 H 8.6 O 9.9%. found: C 81.2 H 8.6 O 10.0%.

IR: $\nu$=1676, 1683 (C=O), 2851, 2923 (C—N), 3350, 3429 (O—H) cm$^{-1}$.

MS (70 eV): m/e=324 (M$^\oplus$), 105 (100%, M$^\oplus$—$C_8H_{17}$).

The benzoins V summarized in Table I a are prepared using the processes (1) and (2) described under A.1 and A.2 (batch sizes: from 0.05 mole to 1.5 moles) and are characterized in Table Ib.

TABLE 1a

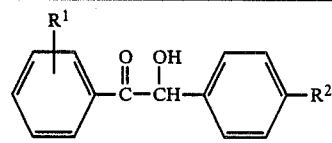

(V)

| Compound | R$^1$ | R$^2$ | Yield[1] (% of theory) | Preparation process |
|---|---|---|---|---|
| V. 1 | H | 4-n-$C_8H_{17}$ | 77 | A |
| V. 2 | 4-n-$C_8H_{17}$ | H | 91 | B |
| V. 3 | H | 4-n-$C_5H_{11}$ | 93 | A |
| V. 4 | 4-n-$C_5H_{11}$ | H | 90 | B |
| V. 5 | 4-n-$C_6H_{13}$ | H | 95 | B |
| V. 6 | 4-n-$C_7H_{15}$ | H | 55 | B |
| V. 7 | 4-n-$C_9H_{21}$ | H | 90 | B |
| V. 8 | 4-n-$C_{10}H_{23}$ | H | 95 | B |
| V. 9 | 4-n-$C_{12}H_{25}$ | H | 96 | B |
| V. 10 | 4-n-$C_{14}H_{29}$ | H | 81 | B |
| V. 11 | 4-n-$C_{15}H_{31}$ | H | 75 | B |
| V. 12 | 2-$CH_3$ | 4-n-$C_8H_{17}$ | 59 | A |
| V. 13 | 3-$CH_3$ | 4-n-$C_8H_{17}$ | 65 | A |
| V. 14 | 4-$CH_3$ | 4-n-$C_8H_{17}$ | 90 | A |
| V. 15 | 3-$CH_3$ | 4-n-$C_{12}H_{25}$ | 83 | A |
| V. 16 | 3-$C_2H_5$ | 4-n-$C_8H_{17}$ | 69 | A |
| V. 17 | 4-$C_2H_5$ | 4-n-$C_8H_{17}$ | 85 | A |
| V. 18 | 2-F | 4-n-$C_8H_{17}$ | 72 | A |
| V. 19 | 3-F | 4-n-$C_8H_{17}$ | 84 | A |
| V. 20 | 4-F | 4-n-$C_6H_{13}$ | 75 | A |
| V. 21 | 4-F | 4-n-$C_7H_{15}$ | 79 | A |
| V. 22 | 4-F | 4-n-$C_8H_{17}$ | 95 | A |
| V. 23 | 4-F | 4-n-$C_9H_{19}$ | 70 | A |
| V. 24 | 4-F | 4-n-$C_{10}H_{21}$ | 82 | A |
| V. 25 | 4-F | 4-n-$C_{12}H_{25}$ | 70 | A |
| V. 26 | 4-F | 4-n-$C_{14}H_{29}$ | 75 | A |
| V. 27 | 4-F | 4-n-$C_{15}H_{31}$ | 77 | A |
| V. 28 | 2-Cl | 4-n-$C_8H_{17}$ | 70 | A |
| V. 29 | 3-Cl | 4-n-$C_8H_{17}$ | 72 | A |
| V. 30 | 4-Cl | 4-n-$C_8H_{17}$ | 82 | A |
| V. 31 | 4-Cl | 4-n-$C_{12}H_{25}$ | 78 | A |
| V. 32 | 2,4-Cl | 4-n-$C_8H_{17}$ | 62 | A |
| V. 33 | 2-Br | 4-n-$C_8H_{17}$ | 65 | A |
| V. 34 | 3-Br | 4-n-$C_8H_{17}$ | 71 | A |
| V. 35 | 4-Br | 4-n-$C_8H_{17}$ | 87 | A |
| V. 36 | 4-Br | 4-n-$C_{12}H_{25}$ | 80 | A |
| V. 37 | 4-Br | 4-n-$C_{15}H_{31}$ | 83 | A |
| V. 38 | 2-$OCH_3$ | 4-n-$C_8H_{17}$ | 52 | A |
| V. 39 | 3-$OCH_3$ | 4-n-$C_8H_{17}$ | 59 | A |
| V. 40 | 4-$OCH_3$ | 4-n-$C_8H_{17}$ | 80 | A |
| V. 41 | 4-$OCH_3$ | 4-n-$C_{12}H_{25}$ | 88 | A |
| V. 42 | 4-$OC_8H_{17}$ | 4-n-$C_8H_{17}$ | 55 | A |
| V. 43 | 4-$SCH_3$ | 4-n-$C_8H_{17}$ | 45 | A |
| V. 44 | 4-$NO_2$ | 4-n-$C_8H_{17}$ | 37 | A |

[1]The yields were obtained under the conditions stated under A.1 and A.2, although these conditions have not been optimized.

TABLE Ib

Characteristic data for the novel benzoins (V)[1]

$$R^1-\underset{}{\bigcirc}-\underset{C}{\overset{O}{\underset{\|}{C}}}-\underset{}{\overset{OH}{\underset{|}{CH}}}-\underset{}{\bigcirc}-R^2 \quad (V)$$

| Compound | Mp. (°C.) | Strongest IR bands ν (cm⁻¹) | |
|---|---|---|---|
| V. 1 | 90 | 1678 | MS: m/e = 219 (100%) M⊕÷(C₆H₅—CO) |
| V. 2 | 74-75 | | |
| V. 3 | 94-95 | 1675 | |
| V. 4 | 66-67 | 1674 | |
| V. 5 | 65-66 | 1674 | MS: m/e = 189 (100%) M⊕÷O=C—⟨⟩—C₆H₁₃ |
| V. 6 | 59-60 | 1677 | |
| V. 7 | 53-54 | 1677 | |
| V. 8 | 70-71 | 1677 | |
| V. 9 | 74-75 | 1676 | |
| V. 10 | 91-92 | | |
| V. 11 | 88-90 | | |
| V. 12 | oil | | |
| V. 13 | oil | | |
| V. 14 | 53-54 | | |
| V. 15 | 60-61 | | |
| V. 16 | oil | | |
| V. 17 | 64-65 | | |
| V. 18 | oil | | |
| V. 19 | oil | | |
| V. 20 | 66-67 | | (2) |
| V. 21 | 60-61 | | (2) |
| V. 22 | 66-67 | 1676 | (2) |
| V. 23 | 63-64 | | (2) |
| V. 24 | 69-70 | | (2) |
| V. 25 | 72-73 | | (2) |
| V. 26 | 74-75 | | (2) |
| V. 27 | 74-75 | | (2) |
| V. 28 | oil | | |
| V. 29 | oil | | |
| V. 30 | 84-85 | | |
| V. 31 | 79-80 | | |
| V. 32 | oil | | |
| V. 33 | oil | | |
| V. 34 | oil | | |
| V. 35 | 92-93 | | |
| V. 36 | 80-81 | | |
| V. 37 | 64-65 | | |
| V. 38 | oil | | |
| V. 39 | oil | | |
| V. 40 | 68-69 | 1670, 1258, 1171 | ¹H—NMR: δ = 3.78 ppm (OCH₃) |
| V. 41 | 57-58 | | |
| V. 42 | oil | | |
| V. 43 | 86-87 | | |
| V. 44 | oil | | |

[1] Benzoins IV purified by column chromatography (mobile phase: CH₂Cl₂) gave correct elemental analyses. The MS, IR, ¹H—NMR and ¹³C—NMR spectra are in accordance with the expected structures.
(2) ¹⁹F—NMR: S = 9.9 ppm (mobile phase: CDCl₃, ref.: fluorobenzene)

B. PREPARATION OF THE DYES (IV)

One example in each case of the preparation of a nickel-, palladium- and platinum-tetraphenyldithiolene complex by the methods due to G. N. Schrauzer et al., J.A.C.S. 87 (1965), 1483–1489 is given below, the procedure used being a modification of the stated method.

The batch sizes vary from 0.005 to 0.3 mole. The yields of crude product are from 70 to 100 percent, depending on the batch size. Column chromatography over silica gel 60 using methylene chloride as the mobile phase ($R_f \approx 0.9$) affords very pure dyes which give correct elemental analysis. The UV/VIS, IR, ¹H-NMR, ¹³C-NMR and MS specra (fragmentation and isotope pattern) are in accordance with the expected structures in every case.

EXAMPLE 1

Bis-(4-n-octyl-dithiobenzil)-nickel (dye 4a)

97.2 g (0.30 mole) of 4-n-octylbenzoin (V.1), 400 g (0.30 mole) of ammonium sulfate and 100 g (0.45 mole) of phosphorous pentasulfide are suspended in 1 l of dioxane, and the suspension is refluxed for 3 hours. After cooling to room temperature, the suspension is filtered, the residue is washed with about 100 ml of dioxane, a solution of 72.0 g (0.30 mole) of nickel chloride hexahydrate in 300 ml of water is added to the filtrate, and the mixture is refluxed for 3 hours. The reaction solution is stirred for about a further 15 hours at room temperature, the crude product being precipitated in the form of fine crystals. This product is filtered off under suction, washed with a little dioxane, then with water and, if required, with a little ethanol to give 130 g (56.5% of theory) of a product which has a small starting spot in thin layer chromatography (silica gel/CH₂Cl₂: $R_f$=0.97; toluene: $R_f$=0.72). Analytically pure bis-(4-n-octyl-dithiobenzil)-nickel is obtained by filtering a solution in methylene chloride over a short silica gel column.

Mp.: 130°–131° C.

C₄₄H₅₂NiS₄ (767) calculated: Ni 7.7%. found: Ni 7.3%.

UV: $\lambda_{max}$=875 nm ($\epsilon$=30,100) in toluene.

EXAMPLE 2

Bis-(4-n-octyl-dithiobenzil)-palladium (dye 4b)

5.20 g (16 millimoles) of 4-n-octylbenzoin (V.1), 4.4 g (32 millimoles) of ammonium sulfate and 7.1 g (32 millimoles) of phosphorus pentasulfide are introduced into 100 ml of dioxane, and the mixture is refluxed for 2 hours. After cooling to room temperature, the suspension is filtered, the residue is washed with a little dioxane, a solution of 2.28 g (7.2 millimoles) of potassium tetrachloropalladate(II) in 40 ml of water is added to the filtrate, and the mixture is refluxed for 2 hours. The stirred reaction solution is cooled slowly to room temperature, a little dioxane is added until the product is precipitated in crystalline form, and the product is then filtered off under suction.

The crude product (4.5 g; 77%) is chromatographed over silica gel 60 using methylene chloride.

Yield: 3.8 g (65% of theory) of bis-(4-n-octyl-dithiobenzil)-palladium (dye 4b).

UV: $\lambda_{max}$=898 nm in methylene chloride.

EXAMPLE 3

Bis-(4-n-octyl-dithiobenzil)-platinum (dye 4c)

2.33 g (7.2 millimoles) of 4-n-octylbenzoin (V.1), 1.00 g (7.5 millimoles) of ammonium sulfate and 2.44 g (11 millimoles) of phosphorus pentasulfide are introduced into 20 ml of dioxane, and the mixture is refluxed for 2 hours. After cooling to room temperature, the suspension is filtered, the residue is washed with a little dioxane, a solution of 0.50 g (1.2 millimoles) of potassium tetrachloroplatinate(II) in 6.5 ml of water is added to the filtrate, and the mixture is refluxed for 2 hours. The violet reaction solution is stirred for not less than a further 2 hours at room temperature. A little dioxane is added to the oily suspension until a violet, finely crystalline substance is precipitated. The solid is filtered off under suction and taken up in methylene chloride, the solution is filtered over silica gel 60, the solvent is stripped off and the residue is dried under reduced pressure to give 1.10 g of violet crude product.

Column chromatography over silica gel 60 using methylene chloride as the mobile phase gives a product which is pure according to thin layer chromatography (silica gel/toluene: $R_f=0.95$, $CH_2Cl_2$: $R_f=0.98$).

Yield: 0.9 g (83% of theory) of bis-(4-n-octyl-dithiobenzil)-platinum.

Mp.: 136°–139° C.

$C_{44}H_{52}S_4Pt$ (903) calculated: Pt 21.6%. found: Pt 21.0%.

UV: $\lambda_{max}=815$ nm in methylene chloride.

EXAMPLE 4

Bis-(4-n-octyl-4'-fluorodithiobenzil)-nickel (dye 19a)

6.84 g (20 millimoles) of 4-n-octyl-4'-fluorobenzoin (V.21), 4.0 g (30 millimoles) of ammonium sulfate and 6.66 g (30 millimoles) of phosphorus pentasulfide are suspended in 30 ml of dioxane, and the suspension is refluxed for 2 hours. After cooling to room temperature, the suspension is filtered, the residue is washed with about 10 ml of dioxane, a solution of 2.4 g (10 millimoles) of nickel(II) chloride hexahydrate in 10 ml of water is added to the filtrate, and the mixture is refluxed for 2 hours. The reaction solution is then stirred for about a further 2 hours at room temperature, the crude product being precipitated in the form of fine crystals. This product is filtered off under suction, washed with a little dioxane, then with water and finally with a little ethanol. The crude product (5.0 g; 62%) has a small starting spot in the thin layer chromatogram (silica gel/$CH_2Cl_2$: $R_f=0.90$). Column chromatography over silica gel 60 using methylene chloride as the mobile phase gives 2.3 g (28.6% of theory) of the analytically pure complex (19a).

Mp.: 154°–155° C.

$C_{44}H_{50}F_2NiS_4$ (803) calculated: C 65.8 H 6.2 F 4.7 S 15.9 Ni 7.4%. found: C 66.1 H 6.4 F 4.7 S 15.6 Ni 6.8%.

UV: $\lambda_{max}=870$ nm ($\epsilon=31554$) in toluene; $\lambda_{max}=873$ nm ($CH_2Cl_2$).

IR (KBr): $\nu=2924$, 2852, 1596, 1504, 1360 (s), 1233, 1144, 890, 829 cm$^{-1}$.

$^{19}$F-NMR (CDCl$_3$): $\delta=-111.0$ ppm (monofluoropentachloroethane).

EXAMPLE 5

Bis-(4-n-octyl-4'-fluorodithiobenzil)-palladium (dye 19b)

2.74 g (8.0 millimoles) of 4-n-octyl-4'-fluorobenzoin (V.21), 1.1 g (8.3 millimoles) of ammonium sulfate and 2.67 g (12 millimoles) of phosphorus pentasulfide are suspended in 40 ml of dioxane, and the suspension is refluxed for 2 hours. After cooling to room temperature, the suspension is filtered, the residue is washed with about 5 ml of dioxane, a solution of 1.27 g (4.0 millimoles) of potassium tetrachloropalladate(II) in 10 ml of water is added to the filtrate, the mixture is refluxed for 2 hours and then cooled to room temperature, after which the finely crystalline precipitate is filtered off and washed with a little dioxane and water. The crude product (3.0 g, 88%) is taken up in methylene chloride, and the solution is chromatographed over silica gel 60.

Yield: 1.1 g (32% of theory) of palladium complex (19b).

UV: $\lambda_{max}=898$ nm in toluene.

EXAMPLE 6

Bis-(4-n-octyl-4'-fluorodithiobenzil)-platinum (dye 19c)

0.89 g (2.6 millimoles) of 4-n-octyl-4'-fluorobenzoin (V.21), 0.34 g (2.6 millimoles) of ammonium sulfate and 0.82 g (5.2 millimoles) of phosphorus pentasulfide are suspended in 20 ml of dioxane, the suspension is refluxed for 2 hours, cooled to room temperature and then filtered, the residue is washed with a few milliliters of dioxane, a solution of 0.50 g (1.2 millimoles) of potassium tetrachloroplatinate(II) in 6.5 ml of water is added to the filtrate, and the mixture is refluxed for 2 hours. It is cooled to room temperature, after which the product is washed with a little cold dioxane, the residue is taken up in methylene chloride and the solution is filtered over a short silica gel column (height of packing about 5 cm). 0.45 g (40%) of the pure platinum complex (silica gel/$CH_2Cl_2$: $R_f=0.90$) are obtained, the following characteristic data being determined for the product:

Mp.: 165°–166° C.

$C_{44}H_{50}F_2PtS_4$ (939) calculated: C 56.2 H 5.3 F 4.1 S 13.6 Pt 20.8%. found: C 56.7 H 5.8 F 3.9 S 13.0 Pt 20.4%.

UV: $\lambda_{max}=814$ nm ($\epsilon=47210$) in toluene; $\lambda_{max}=817$ ($CH_2Cl_2$).

IR (KBr): $\nu=2924$, 2852, 1597, 1505, 1407, 1363 (s), 1233, 1148, 887, 829 cm$^{-1}$.

$^{19}$F-NMR (COCl$_3$): $\delta=-111$ ppm (monofluoropentachloroethane).

The dyes of the formula (IV) stated in Table 2a are prepared as described in Examples 1 to 6.

The dyes are characterized in Table 2b by the absorption maximum and, if appropriate, by the molar extinction coefficient and the melting point.

Chromatography over silica gel 60 using methylene chloride ($R_f \approx 0.9$) gives analytically pure complex dyes.

TABLE 2 A

Dithiolene complex dyes

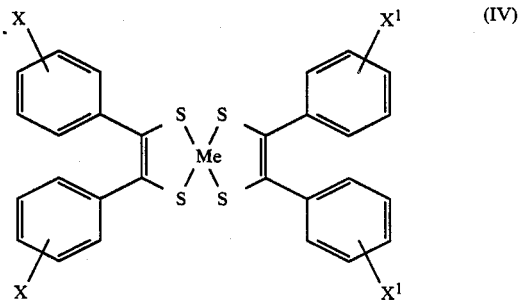

(IV)

| Dye | Me | One X and One X$^1$ | the other X and the other X$^1$ |
|---|---|---|---|
| 1a | Ni | | |
| 1b | Pd | 4-n-C$_5$H$_{11}$ | H |
| 1c | Pt | | |
| 2a | Ni | | |
| 2b | Pd | 4-n-C$_6$H$_{13}$ | H |
| 2c | Pt | | |
| 3a | Ni | | |
| 3b | Pd | 4-n-C$_7$H$_{15}$ | H |
| 3c | Pt | | |

TABLE 2 A-continued
Dithiolene complex dyes

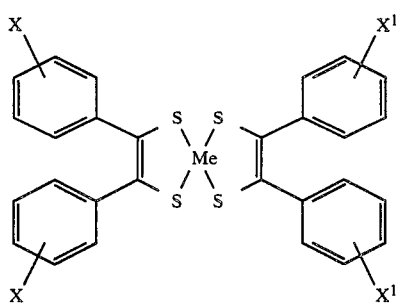 (IV)

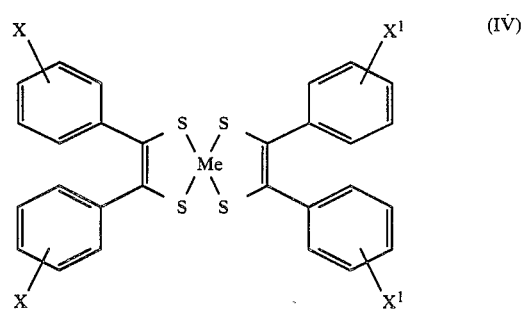 (IV)

| Dye | Me | One X and One $X^1$ | the other X and the other $X^1$ |
|---|---|---|---|
| 4a | Ni | | |
| 4b | Pd | 4-n-$C_8H_{17}$ | H |
| 4c | Pt | | |
| 5a | Ni | | |
| 5b | Pd | 4-n-$C_9H_{19}$ | H |
| 5c | Pt | | |
| 6a | Ni | | |
| 6b | Pd | 4-n-$C_{10}H_{21}$ | H |
| 6c | Pt | | |
| 7a | Ni | | |
| 7b | Pd | 4-n-$C_{12}H_{25}$ | H |
| 7c | Pt | | |
| 8a | Ni | | |
| 8b | Pd | 4-n-$C_{14}H_{29}$ | H |
| 8c | Pt | | |
| 9a | Ni | | |
| 9b | Pd | 4-n-$C_{15}H_{31}$ | H |
| 9c | Pt | | |
| 10a | Ni | | |
| 10b | Pd | 4-n-$C_8H_{17}$ | 2-$CH_3$ |
| 10c | Pt | | |
| 11a | Ni | | |
| 11b | Pd | 4-n-$C_8H_{17}$ | 3-$CH_3$ |
| 11c | Pt | | |
| 12a | Ni | | |
| 12b | Pd | 4-n-$C_8H_{17}$ | 4-$CH_3$ |
| 12c | Pt | | |
| 13a | Ni | | |
| 13b | Pd | 4-n-$C_{12}H_{25}$ | 4-$CH_3$ |
| 13c | Pt | | |
| 14a | Ni | | |
| 14b | Pd | 4-n-$C_8H_{17}$ | 3-$C_2H_5$ |
| 14c | Pt | | |
| 15a | Ni | | |
| 15b | Pd | 4-n-$C_8H_{17}$ | 4-$C_2H_5$ |
| 15c | Pt | | |
| 16a | Ni | | |
| 16b | Pd | 4-n-$C_8H_{17}$ | 2-F |
| 16c | Pt | | |
| 17a | Ni | | |
| 17b | Pd | 4-n-$C_8H_{17}$ | 3-F |
| 17c | Pt | | |
| 18a | Ni | | |
| 18b | Pd | 4-n-$C_6H_{13}$ | 4-F |
| 18c | Pt | | |
| 19a | Ni | | |
| 19b | Pd | 4-n-$C_7H_{15}$ | 4-F |
| 19c | Pt | | |
| 20a | Ni | | |
| 20b | Pd | 4-n-$C_8H_{17}$ | 4-F |
| 20c | Pt | | |
| 21a | Ni | | |
| 21b | Pd | 4-n-$C_9H_{19}$ | 4-F |
| 21c | Pt | | |
| 22a | Ni | | |
| 22b | Pd | 4-n-$C_{10}H_{21}$ | 4-F |
| 22c | Pt | | |
| 23a | Ni | | |
| 23b | Pd | 4-n-$C_{12}H_{25}$ | 4-F |
| 23c | Pt | | |
| 24a | Ni | | |
| 24b | Pd | 4-n-$C_{14}H_{29}$ | 4-F |
| 24c | Pt | | |
| 25a | Ni | | |
| 25b | Pd | 4-n-$C_{15}H_{31}$ | 4-F |
| 25c | Pt | | |
| 26a | Ni | | |
| 26b | Pd | 4-n-$C_8H_{17}$ | 2-Cl |
| 26c | Pt | | |
| 27a | Ni | | |
| 27b | Pd | 4-n-$C_8H_{17}$ | 3-Cl |
| 27c | Pt | | |
| 28a | Ni | | |
| 28b | Pd | 4-n-$C_8H_{17}$ | 4-Cl |
| 28c | Pt | | |
| 29a | Ni | | |
| 29b | Pd | 4-n-$C_8H_{17}$ | 2,4-Cl |
| 29c | Pt | | |
| 30a | Ni | | |
| 30b | Pd | 4-n-$C_{12}H_{25}$ | 4-Cl |
| 30c | Pt | | |
| 31a | Ni | | |
| 31b | Pd | 4-n-$C_8H_{17}$ | 2-Br |
| 31c | Pt | | |
| 32a | Ni | | |
| 32b | Pd | 4-n-$C_8H_{17}$ | 3-Br |
| 32c | Pt | | |
| 33a | Ni | | |
| 33b | Pd | 4-n-$C_8H_{17}$ | 4-Br |
| 33c | Pt | | |
| 34a | Ni | | |
| 34b | Pd | 4-n-$C_{12}H_{25}$ | 4-Br |
| 34c | Pt | | |
| 35a | Ni | | |
| 35b | Pd | 4-n-$C_{15}H_{31}$ | 4-Br |
| 35c | Pt | | |
| 36a | Ni | | |
| 36b | Pd | 4-n-$C_8H_{17}$ | 2-$OCH_3$ |
| 36c | Pt | | |
| 37a | Ni | | |
| 37b | Pd | 4-n-$C_8H_{17}$ | 3-$OCH_3$ |
| 37c | Pt | | |
| 38a | Ni | | |
| 38b | Pd | 4-n-$C_8H_{17}$ | 4-$OCH_3$ |
| 38c | Pt | | |
| 39a | Ni | | |
| 39b | Pd | 4-n-$C_{12}H_{25}$ | 4-$OCH_3$ |
| 39c | Pt | | |
| 40a | Ni | | |
| 40b | Pd | 4-n-$C_8H_{17}$ | 4-$OC_8H_{17}$ |
| 40c | Pt | | |
| 41a | Ni | | |
| 41b | Pd | 4-n-$C_8H_{17}$ | 4-$SCH_3$ |
| 41c | Pt | | |
| 42a | Ni | | |
| 42b | Pd | 4-n-$C_8H_{17}$ | 4-$NO_2$ |
| 42c | Pt | | |

TABLE 2 b
Dithiolene complex dyes, physical data
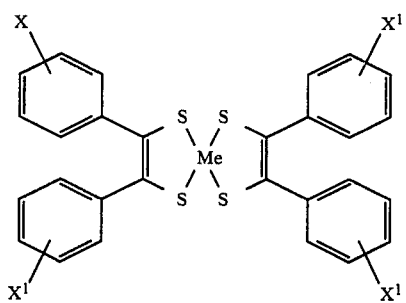
(IV)
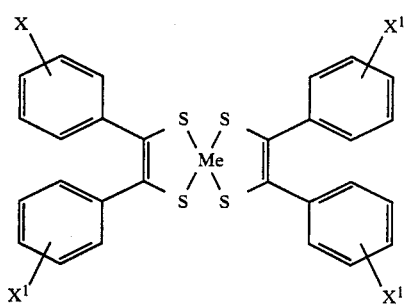
(IV)
λmax measured methylene chloride or toluene [(1)]
| Dyes | λmax/nm ($\epsilon \cdot 10^3$) | Mp. [°C.] |
|---|---|---|
| 1a | 871 (27,4) | 164–166 |
| 1b | 897 | 181–183 |
| 1c | 814 | 185–188 |
| 2a | 875 (30,4) | 148–150 |
| 2b | 896 | |
| 2c | 817 (52,6) | 158–159 |
| 3a | 870 (22,3) | 142–143 |
| 3b | 897 | |
| 3c | 810 (48,8) | 156–157 |
| 4a | 875 (31,7) | 130–131 |
| 4b | 898 | |
| 4c | 817 (57,7) | 136–139 |
| 5a | 865 (25,1) | 134–135 |
| 5b | 897 | |
| 5c | 818 (51,0) | 142–143 |
| 6a | 870[(1)] (32,1) | 126–127 |
| 6b | 895 | |
| 6c | 812 (47,7) | 128–132 |
| 7a | 870 (31,6) | 118–120 |
| 7b | 896 | |
| 7c | 812 (51,6) | 123–127 |
| 8a | 868 (30,0) | 112–113 |
| 8b | 895 | |
| 8c | 811 (43,8) | 113–114 |
| 9a | 870 (31,3) | 110–111 |
| 9b | 896 | |
| 9c | 811 (49,9) | 124–125 |
| 10a | | |
| 10b | | |
| 10c | | |
| 11a | | |
| 11b | | |
| 11c | | |
| 12a | 883 (33,3) | 158–159 |
| 12b | | |
| 12c | 822 (48,9) | 172–173 |
| 13a | 885 (33,5) | 142–143 |
| 13b | | |
| 13c | 828 (52,5) | 149–150 |
| 14a | 880 (26,1) | oil |
| 14b | | |
| 14c | 822 (48,7) | 108–109 |
| 15a | 890 (33,5) | 179–180 |
| 15b | | |
| 15c | 829 (50,9) | 194–195 |
| 16a | | |
| 16b | | |
| 16c | | |
| 17a | 868 | |
| 17b | 895 | |
| 17c | 812 | |
| 18a | 868 | |
| 18b | 895 | |
| 18c | 812 | |
| 19a | | |
| 19b | | |
| 19c | | |
| 20a | 870[(1)] (31,6) | 154–155 |
| 20b | 902[(1)] | |
| 20c | 815[(1)] (47,2) | 160–162 |
| 21a | 875 (29,7) | 138–140 |
| 21b | 900 | |
| 21c | 817 (47,9) | 144–145 |
| 22a | 873 (31,4) | 140–141 |
| 22b | 899 | |
| 22c | 814 (48,9) | 152–153 |
| 23a | 865 (26,6) | 128–129 |
| 23b | 900 | |
| 23c | 819 (42,9) | 140–141 |
| 24a | 868 (29,9) | 125–126 |
| 24b | 896 | |
| 24c | 810 (47,8) | 134–135 |
| 25a | 873 (28,1) | 121–122 |
| 25b | 901 | |
| 25c | 814 (47,1) | 125–126 |
| 26a | | |
| 26b | | |
| 26c | | |
| 27a | | |
| 27b | | |
| 27c | | |
| 28a | 873 (30,4) | 161–162 |
| 28b | 904 | |
| 28c | 815 (51,6) | 192–193 |
| 29a | | oil |
| 29b | | oil |
| 29c | | oil |
| 30a | 863 (30,9) | 150–151 |
| 30b | 901 | |
| 30c | 815 (51,5) | 166–168 |
| 31a | | oil |
| 31b | | oil |
| 31c | 789 | oil |
| 32a | | |
| 32b | | |
| 32c | | |
| 33a | 883 (31,5) | 176–177 |
| 33b | 908 | |
| 33c | 818 (55,5) | 204–205 |
| 34a | 878 (31,9) | 156–157 |
| 34b | 907 | |
| 34c | 820 (53,5) | 177–178 |
| 35a | 880 (34,0) | 150–151 |
| 35b | 906 | |
| 35c | 820 (53,8) | 170–171 |
| 36a | | |
| 36b | | |
| 36c | | |
| 37a | | |
| 37b | | |
| 37c | | |
| 38a | 908 (33,9) | 140–145 |
| 38b | | |
| 38c | 834 (43,4) | 160–165 |
| 39a | 910 (34,6) | 152–154 |
| 39b | | |
| 39c | 849 (50,1) | 164–165 |
| 40a | | |
| 40b | | |
| 40c | | |
| 41a | | 157–158 |
| 41b | | |

TABLE 2 b-continued
Dithiolene complex dyes, physical data

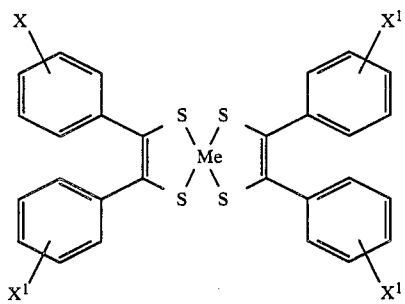
(IV)

λmax measured methylene chloride or toluene [(1)]

| Dyes | λmax/nm (ε · 10³) | Mp. [°C.] |
|---|---|---|
| 41c | | 168–169 |
| 42a | | |
| 42b | | |
| 42c | | |

C.
PREPARATION OF THE OPTICAL RECORDING MATERIAL

EXAMPLE 7

Two 1.2 mm thick polycarbonate disks having a diameter of 120 mm and a central hole with a diameter of 15 mm are cleaned with alcohol, and coated with a 0.3 μm thick photopolymer subbing layer under cleanroom conditions. The photopolymer is cured with UV light, after which a solution of 2 g of the dye 4c and 1.3 g of a 70:30 methyl methacrylate/methacrylic acid copolymer in 200 ml of ethyl acetate is applied onto the disks by the whirler coating method at 4800 rpm. After drying, the layer is 0.26 μm thick. A 0.03 μm thick aluminum mirror is applied on top of the dye layer in a vapor deposition apparatus under reduced pressure. A 1.2 μm thick protective layer is applied on top of the aluminum mirror by whirler coating using polystyrene in xylene.

The two disks are bonded together via a suitable spacer rings to form a sandwich with the coated sides facing inward, so that an air gap of 0.4 mm remains. Individual holes about 1 μm in size are written into the active layer using an AlGaAs laser (λ=820 nm) mounted on a rotating table. The sensitivity of the layer is better than 1 nJ/hole, and an excellent signal/noise ratio is obtained when the points are read.

We claim:
1. A tetraphenyldithiolene complex of the formula

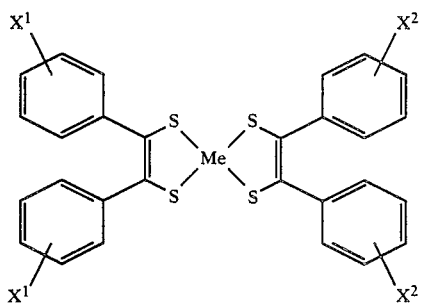

where one radical $X^1$ and one radical $X^2$ are each straight-chain or branched $C_{5-30}$ alkyl in the 4-position, the other radical $X^1$ and the other radical $X^2$ are each fluorine, chlorine or bromine in the 2-, 3- or 4-position, and Me is nickel, palladium or platinum.

2. The tetraphenyldithiolene complex of claim 1, wherein one radical $X^1$ and one radical $X^2$ are each straight-chain or branched $C_{8-24}$ alkyl.

3. The tetraphenyldithiolene complex of claim 1, wherein Me is platinum.

4. A tetraphenyldithiolene complex of the formula

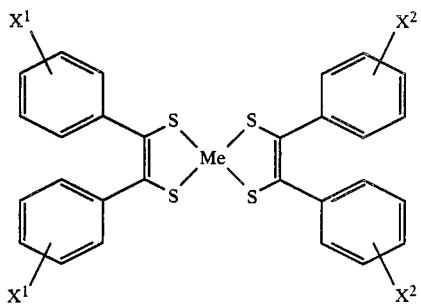

were one radical $X^1$ and one radical $X^2$ are each straight-chain or branched $C_{14-30}$ alkyl in the 4-position, the other radical $X^1$ and the other radical $X^2$ are each hydrogen, $C_{1-12}$ alkyl, $C_{1-12}$ alkoxy, fluorine, chlorine or bromine in the 2-, 3-, 4-position, and Me is nickel, palladium or platinum.

5. The tetraphenyldithiolene complex of claim 4, wherein the other radical $X^1$ and the other radical $X^2$ are each methyl, ethyl, methoxy, ethoxy, fluorine, bromine or chlorine.

6. The tetraphenyldithiolene complex of claim 4, wherein Me is platinum.

* * * * *